United States Patent
van der Zaag et al.

(10) Patent No.: US 12,165,319 B2
(45) Date of Patent: Dec. 10, 2024

(54) APPARATUS FOR DIAGNOSTIC IMAGE ACQUISITION DETERMINATION

(71) Applicant: KONINKLIJKE PHILIPS N.V., Eindhoven (NL)

(72) Inventors: Pieter Jan van der Zaag, Waalre (NL); Wilhelmus Franciscus Johannes Verhaegh, Asten (NL); Jochen Keupp, Rosengarten (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 385 days.

(21) Appl. No.: 17/777,713

(22) PCT Filed: Nov. 17, 2020

(86) PCT No.: PCT/EP2020/082312
§ 371 (c)(1),
(2) Date: May 18, 2022

(87) PCT Pub. No.: WO2021/099280
PCT Pub. Date: May 27, 2021

(65) Prior Publication Data
US 2023/0028306 A1    Jan. 26, 2023

(30) Foreign Application Priority Data
Nov. 19, 2019    (EP) .................................... 19210005

(51) Int. Cl.
*G06T 7/00*    (2017.01)

(52) U.S. Cl.
CPC .. *G06T 7/0012* (2013.01); *G06T 2207/30096* (2013.01); *G06T 2207/30204* (2013.01)

(58) Field of Classification Search
CPC ......... G06T 7/0012; G06T 2207/30096; G06T 2207/30204
USPC .......................................................... 382/128
See application file for complete search history.

(56) References Cited

U.S. PATENT DOCUMENTS

| 7,490,085 | B2* | 2/2009 | Walker | A61B 5/395 |
| | | | | 600/125 |
| 10,646,156 | B1* | 5/2020 | Schnorr | G16H 30/40 |
| 2004/0120557 | A1* | 6/2004 | Sabol | G09B 23/28 |
| | | | | 382/128 |

(Continued)

FOREIGN PATENT DOCUMENTS

WO    2018083467 A1    5/2018

OTHER PUBLICATIONS

N.M. de Souza "Monitoring Response to Therapy" Proc. Intl.Soc. Mag. Reson. Med. 2018.

(Continued)

*Primary Examiner* — Allen H Nguyen

(57) ABSTRACT

The present invention relates to an apparatus (10) for diagnostic image acquisition, comprising: an input unit (20); a processing unit (30); and an output unit (40). The input unit is configured to receive a data value relating to at least one biomarker in a measurement blood sample of a patient. The processing unit is configured to determine a time to acquire a diagnostic image of the patient, wherein the determination comprises utilization of the data value. The output unit is configured to output an indication of the time to acquire the diagnostic image of the patient.

15 Claims, 4 Drawing Sheets

(56) References Cited

U.S. PATENT DOCUMENTS

2016/0032396 A1    2/2016  Diehn et al.
2020/0178875 A1*   6/2020  Ojeda ................... A61B 5/374
2021/0098129 A1*   4/2021  Neumann .............. G06N 20/00

OTHER PUBLICATIONS

International Search Report and Written Opinion from PCT/EP2020/082312 mailed Feb. 2, 2021.
Kaufmann et al "Recommendations from an International Consensus Conference on the Current Status and Future of Neoadjuvant Systemic Therapy in Primary Breast Cancer" Annals of Surgical Oncology, vol. 19, No. 5, p. 1508-1516 (Dec. 23, 2011).
Wikipedia "Response Evaluation Criteria in Solid Tumors" Feb. 11, 2019.
Therasse et al "New Guidelines to Evaluate the Response to Treatment in Solid Tumors" Journal of the National Cancer Institute vol. 92, No. 3, Feb. 2, 2000 p. 205-216.

* cited by examiner

APPARATUS FOR DIAGNOSTIC IMAGE ACQUISITION DETERMINATION

CROSS REFERENCE TO RELATED APPLICATIONS

This application is a U.S. national phase application of International Application No. PCT/EP2020/082312 filed Nov. 17, 2020, which claims the benefit of EP application Ser. No. 19/210,005.5 filed Nov. 19, 2019 and is incorporated herein by reference.

FIELD OF THE INVENTION

The present invention relates to an apparatus for diagnostic image acquisition determination, a system for diagnostic image acquisition determination, an image acquisition system, a method for diagnostic image acquisition determination, as well as to a computer program element and a computer readable medium.

BACKGROUND OF THE INVENTION

Currently, in so-called neo-adjuvant therapy (NAT), all cancer patients receive a standard or standardized drug therapy regime involving a form of chemotherapy and/or radiation therapy and/or ablation treatment. Currently, imaging is the golden standard to assess the efficacy of a treatment (be it drugs, radiation, ablation) to see if the tumour responds to treatment and shrinks, remains unaltered or even grows further (regression, stable disease or progression). The ISMRM-2018 abstract '*Monitoring response to therapy*' by N. M. deSouza mentions that it may be advantageous to turn to imaging during radiotherapy to adapt therapy plan. However, during the neo-adjuvant therapy, in which a patient is given medication to shrink the tumour to enable more successful surgery, one does not know what the optimal time point would be for imaging in order to check the efficacy of the treatment given. This is because the time course of the response may be different for each individual patient. In current clinical routine, imaging is typically applied mid-therapy, following a fixed therapy regimen.

The disadvantages of using a fixed point in time for imaging assessment of the patient's response to therapy are:
  patients who respond quickly to therapy may continue with therapy for too long before undergoing surgery, and may experience unnecessary adverse therapy effects;
  patients who respond slowly to therapy are imaged too early, and have to undergo another imaging procedure later to confirm sufficient tumour shrinkage; and
  patients who respond poorly, or not at all, have to wait too long for confirmation by imaging, and have to wait too long for another therapy regimen to be chosen, while possibly suffering side effects.

Hence, it would be advantageous to perform imaging at a suitable moment in time for individual patients, enabling therapy to be stopped earlier when surgical intervention is possible or enabling a new therapy regime to be adopted for patients who are not responding to the current therapy regime.

SUMMARY OF THE INVENTION

It would be advantageous to have improved means of determining when to image a patient to determine if they are responding to therapy, which the present disclosure indicates can be derived based on at least one biomarker from one or more blood samples. The object of the present invention is solved with the subject matter of the independent claims, wherein further embodiments are incorporated in the dependent claims. It should be noted that the following described aspects and examples of the invention apply also to the apparatus for diagnostic image acquisition determination, the system for diagnostic image acquisition determination, the image acquisition system, the method for diagnostic image acquisition determination, as well as to the computer program element and a computer readable medium.

In a first aspect, there is provided an apparatus for diagnostic image acquisition, comprising:
  an input unit;
  a processing unit; and
  an output unit.

The input unit is configured to receive a data value relating to at least one biomarker in a measurement blood sample of a patient. The processing unit is configured to determine a time to acquire a diagnostic image of the patient, wherein the determination comprises utilization of the data value. The output unit is configured to output an indication of the time to acquire the diagnostic image of the patient.

In this manner, one or more biomarkers can be monitored for example over the time course of the NAT and the determination made when diagnostic image scanning could favorably be done to determine if indeed the patient is responding or not responding to therapy. It has been established, the change in value associated with one or more biomarkers can be correlated with the tumour response, and thus monitoring of the biomarker or biomarkers in the blood of the patient can be used to determine when an image scan of the patient is warranted. The apparatus also finds utility for example in the monitoring of a cancer patents after surgery, where it can be determined when imaging should be done as the patient may show relapse, based on liquid biopsy information in the form of one or more biomarkers.

In other words, an optimum time to acquire diagnostic imagery of a patient can be determined from information from biomarkers in blood of the patient taken during the course of therapy. This can be used to trigger that image acquisition be carried out, or enable a medical practitioner better to make that decision. In the following, an image acquisition to control therapy response is called "diagnostic image".

Thus the output unit can output an indication of a proposed optimal time to acquire the diagnostic image of the patient to assess the patient response as early as possible.

In an example, blood samples of the patient can be taken at different time points in a therapy, and data values relating to the at least one biomarker in each of these data samples can be received by the input unit. Thus, a time history of the data value relating to the at least one biomarker can be determined, enabling a projection or prediction into the future and also enabling error analysis to provide statistical relevance to the accuracy of the present data value and of any predicted future data value, which can be used to determine the time to acquire a diagnostic image of the patient.

It is also to be noted that the input unit can receive also general information available on the tumor (sub-)type and type of therapy (drug type, radiation dose and the like) relating to the patient. This information, along with the data value or values can be utilised by the processing unit to determine the time to acquire a diagnostic image of the patient.

In an example, the input unit is configured to receive a baseline data value relating to the at least one biomarker in a baseline blood sample of the patient, and wherein the determination of the time to acquire the diagnostic image comprises utilization of the baseline data value.

Thus, a baseline blood sample, taken for example at the time t=0 when the patient begins therapy, can be acquired, and a data value relating to one or more biomarkers in the blood can be determined. Then, as the patient undergoes therapy, further blood samples can be taken from the patient and analysed to determine data values relating to the one or more biomarkers in the blood. The apparatus is then provided with the data value associated with the one or more biomarkers of the baseline sample, and the data value associated with the one or more biomarkers of the newly acquired blood sample. Then, the baseline data value and the newly derived data value can be utilised to determine if a change in the biomarker composition indicates that the patient is responding well to therapy or not (yet) responding, enabling a determination to be made which time point would be optimal for the patient to undergo image scanning for confirmation of the related tumour size changes. The baseline data value in combination with the newly derived data value can also to be utilised to determine an expected change in size of the tumour, that could be indicative that the patient is responding well to therapy or not yet responding, again enabling a determination to be made of the time point that would be optimal for the patient to undergo image scanning for confirmation of the tumour size change.

In this manner, an optimum time to acquire an image of the patient can be determined. This time point could be immediately after the last blood draw, but from the change in biomarker values over time a prediction can be made about an optimum time point for imaging assessment in the future.

In summary, the present invention is based on the novel and inventive insight that from biomarker data in a patient's blood sample an optimum instant for diagnostic imaging. The technical effect achieved by the present invention amounts to the determination of an optimum trigger for diagnostic imaging after treatment that finds a balance between (i) imaging at a sufficient delay from treatment at which there is a high-likelihood that tumour volume can be accurately assessed from the image information (ii) avoid imaging too early that only puts a burden on the patient to be examined and assessment of tumour volume is unlikely to be successful and (iii) avoiding imaging at a late stage so that for a non-responding patient therapy is not changed or changed (too) late. That is, the technical effect of the present invention is to appropriately time imaging for improved image quality in that tumour volume may be reliably and quantitatively assessed form the image information. The image information forms an intermediate technical result that serves to support the physician to decide on how to continue treatment.

In an example, the determination of the time to acquire the diagnostic image comprises a comparison of the data value with at least one threshold data value.

In an example, the processing unit is configured to determine the at least one threshold data value, wherein the determination of the at least one threshold data value comprises utilization of the baseline data value.

Thus, a threshold data value can be derived from the baseline data value, and if the newly determined data value falls below or rises above certain threshold data values, a prediction can be made that the tumour is expected to be shrunk by a size that can now be resolved by an imaging unit, or shrunk by a size that is an indicator of positive response to therapy, or that the tumour is growing. The prediction can then be used to recommend image scanning of the patient at a suitable time point, to confirm these findings.

In an example, each threshold data value of the at least one threshold data value is calculated as a proportion of the baseline data value.

In an example, the determination of the time to acquire the diagnostic image comprises a determination that the data value is equal to or less than at least one first threshold data value of the at least one threshold data value.

In an example, the determination of the time to acquire the diagnostic image comprises a determination that the data value is equal to or greater than a second threshold data value of the at least one threshold data value.

In an example, the determination of the at least one threshold data value comprises a determination of one or more threshold data values indicative of a dimension change or volume change of a tumour of the patient.

It has been established that a data value associated with one or more biomarkers scales with a volume of a tumour, and thus the change in the value associated with one or more biomarkers as the patient undergoes therapy can be used when the change is significant enough to warrant an image scan carried out. In this manner, threshold values can be determined relating to volume or dimension changes of a tumour that can correlate back to a change in data value with respect to a baseline data value—thereby providing a threshold data value.

In an example, a threshold data value of the at least one data threshold data value is calculated as 0.34 of the baseline data value.

In this manner, for a uniform 30% linear dimension reduction of a tumour in all 3 dimensions, the anticipated data value relating to the one or more biomarker is then 0.34 that of the baseline data value ($0.7^3=0.34$).

In an example, a threshold data value of the at least one data threshold data value is calculated as 1.73 of the baseline data value; and/or a threshold data value of the at least one data threshold data value is calculated as 1.33 of the baseline data value.

In this manner, for a uniform 20% linear dimension increase of a tumour in all 3 dimensions, the anticipated data value relating to the one or more biomarker is then 1.73 that of the baseline data value ($1.2^3=1.73$).

In an example, the input unit is configured to receive imaging resolution information relating to at least one image acquisition unit configured for the diagnostic image acquisition. Determination of one or more threshold data value of the at least one threshold data value can then comprise utilization of the imaging resolution information.

In this manner, a threshold data value can be determined on the basis of the baseline data value and the resolution of a scanner such as an MRI system or CT system, such that a change in data value with respect to the baseline data value would indicate that for a typically sized tumour the change in data value would indicate that a change in size of the tumour detectable by the scanner has occurred.

In an example, a threshold data value of the at least one data threshold data value is calculated as 0.73 of the baseline data value In this manner, a 10% reduction in size ($0.9^3=0.73$) is anticipated from the change in data value relating to the one or more biomarker, and for standard tumour at the onset of therapy of approximately 3 cm, a change in dimension of 3 mm is within the resolving power of imaging systems such as MRI and CT.

In a second aspect, there is provided a system for diagnostic image acquisition, comprising:
an analysis unit; and
an apparatus according to the first aspect.

The analysis unit is configured to analyze a blood sample of a patient and determine a data value relating to at last one biomarker in the blood sample.

In a third aspect, there is provided an image acquisition system, comprising:
an image acquisition unit; and
an apparatus according to the first aspect, or a system according to the second aspect.

In a fourth aspect, there is provided a method for diagnostic image acquisition, comprising:
c) receiving by an input unit a data value relating to at least one biomarker in a measurement blood sample of a patient:
e) determining by a processing unit a time to acquire a diagnostic image of the patient, wherein the determining comprises utilizing the data value; and
f) outputting by an output unit an indication of the time to acquire the diagnostic image of the patient.

According to another aspect, there is provided a computer program element controlling one or more of the apparatuses or systems as previously described which, if the computer program element is executed by a processing unit, is adapted to perform one or more of the methods as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

To understand the context of the apparatus for diagnostic image acquisition determination, the system for diagnostic image acquisition determination, the image acquisition system, and the method for diagnostic image acquisition determination the following provides relevant information regarding utility of the new techniques described.

Neo-adjuvant therapy (NAT) is that in which a patient is given a therapy (drug, radiation or combination of both) typically done to shrink a tumor so that it would become operable (note that surgery is typically the most common form of curative treatment for cancer). NAT is a very prominent case, where the apparatus, systems and method described here find applicability. However, the apparatus, systems and methods described here also find utility with respect to the period when a patient typically is monitored after (presumably) successful surgery. Currently, a patient is then imaged at multiple time points. In colon cancer in the first 2 years, imaging every 6 months and subsequently every year is carried out by CT to determine if relapse of a tumour is detected. After 5 years, without relapse the patient is considered clean/cured. Thus, for the situation for a patient after surgery, a blood sample or blood samples in the form of one or more liquid biopsies can be used to provide associated biomarker data to determine when a relapse seems to have occurred, which could then be confirmed by diagnostic imaging.

The following, then relates to details of specific embodiments that can be used in these manners.

Figure 1:
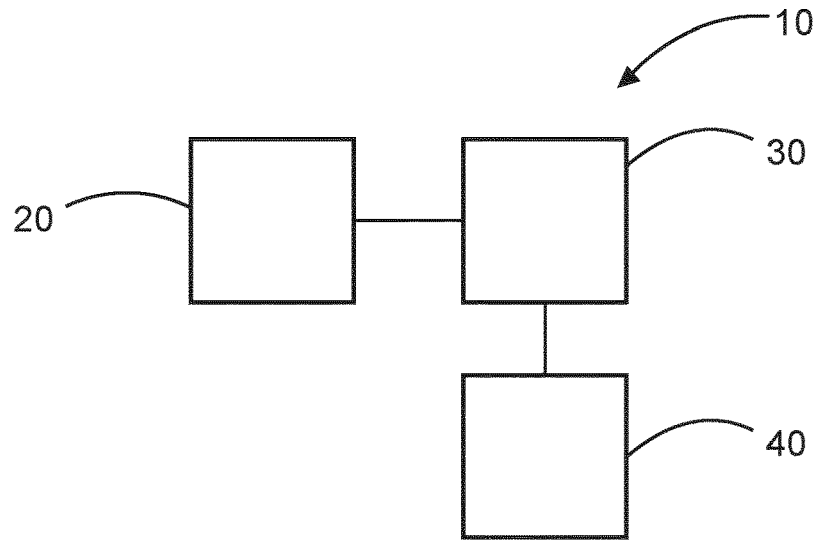
FIG. 1 shows a schematic set up of an example of an apparatus for diagnostic image acquisition, a system for diagnostic image acquisition determination.

FIG. 1 shows an example of an apparatus 10 for diagnostic image acquisition. The apparatus comprises an input unit 20, a processing unit 30, and an output unit 40. The input unit is configured to receive a data value relating to at least one biomarker in a measurement blood sample of a patient. The processing unit is configured to determine a time to acquire a diagnostic image of the patient. The determination comprises utilization of the data value. The output unit is configured to output an indication of the time to acquire the diagnostic image of the patient.

In an example, the data value comprises one or more of: ct-DNA (circulating tumour DNA), CTCs (Circulating Tumour Cells), Exosomes, Platelets.

In an example, the data value comprises a summation of one or more biomarkers.

In an example, the data value comprises a mutant allele frequency.

In an example, the data value comprises a summed mutant allele frequency.

In an example, the data value comprises a summation over all mutant allele frequencies.

According to an example, the input unit is configured to receive a baseline data value relating to the at least one biomarker in a baseline blood sample of the patient. The determination of the time to acquire the diagnostic image can then comprise utilization of the baseline data value.

In an example, the baseline data value comprises one or more of: ct-DNA (circulating tumour DNA), CTCs (Circulating Tumour Cells), Exosomes, Platelets.

In an example, the baseline data value comprises a summation of one or more biomarkers.

In an example, the baseline data value comprises a mutant allele frequency.

In an example, the baseline data value comprises a summed mutant allele frequency.

In an example, the baseline data value comprises a sum over mutant allele frequency.

According to an example, the determination of the time to acquire the diagnostic image comprises a comparison of the data value with at least one threshold data value.

According to an example, the processing unit is configured to determine the at least one threshold data value. The determination of the at least one threshold data value can then comprise utilization of the baseline data value.

According to an example, each threshold data value of the at least one threshold data value is calculated as a proportion of the baseline data value.

According to an example, the determination of the time to acquire the diagnostic image comprises a determination that the data value is equal to or less than at least one first threshold data value of the at least one threshold data value.

According to an example, the determination of the time to acquire the diagnostic image comprises a determination that the data value is equal to or greater than a second threshold data value of the at least one threshold data value.

According to an example, the determination of the at least one threshold data value comprises a determination of one or more threshold data values indicative of a dimension change or volume change of a tumour of the patient.

In an example, a threshold data value of the at least one threshold data value is determined as a value indicative of a 30% linear dimension reduction or 66% volume reduction.

According to an example, a threshold data value of the at least one data threshold data value is calculated as 0.34 of the baseline data value.

In an example, a threshold data value of the at least one threshold data value is determined as a value indicative of a 20% linear dimension increase or 73% volume increase.

According to an example, a threshold data value of the at least one data threshold data value is calculated as 1.73 of the baseline data value; and/or a threshold data value of the at least one data threshold data value is calculated as 1.33 of the baseline data value.

According to an example, the input unit is configured to receive imaging resolution information relating to at least one image acquisition unit configured for the diagnostic image acquisition. The determination of one or more threshold data value of the at least one threshold data value can then comprise utilization of the imaging resolution information.

In an example, the input unit is configured to receive information relating to a size of a tumour of the patient when, or close in time to when, the baseline blood was taken from the patient. Thus, the exact size of the tumour at a start point is known and a determination can be made on the data value in comparison with the baseline data value to determine a dimension change of the tumour and determine if the scanner could resolve this change in size or not.

Figure 2:
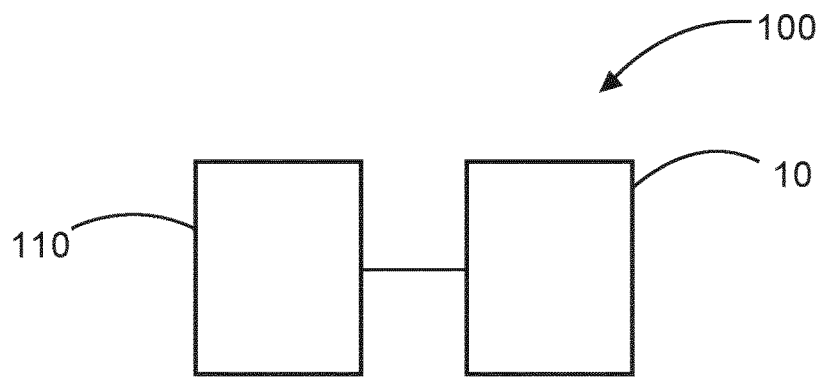
FIG. 2 shows a schematic set up of an example of a system for diagnostic image acquisition determination.

According to an example, a threshold data value of the at least one data threshold data value is calculated as 0.73 of the baseline data value FIG. 2 shows an example of a system 100 for diagnostic image acquisition. The system 100 comprises an analysis unit 110, and an apparatus 10 as described above with respect to FIG. 1. The analysis unit is configured to analyze a blood sample of a patient and determine a data value relating to at last one biomarker in the blood sample.

In an example, the data value comprises one or more of: ct-DNA (circulating tumour DNA), CTCs (Circulating Tumour Cells), Exosomes, Platelets.

In an example, the data value comprises a summation of one or more biomarkers.

In an example, the data value comprises a mutant allele frequency.

In an example, the data value comprises a summed mutant allele frequency.

In an example, the baseline data value comprises a sum over mutant allele frequency.

In an example, the data value comprises a summation over all mutant allele frequencies.

Figure 3:
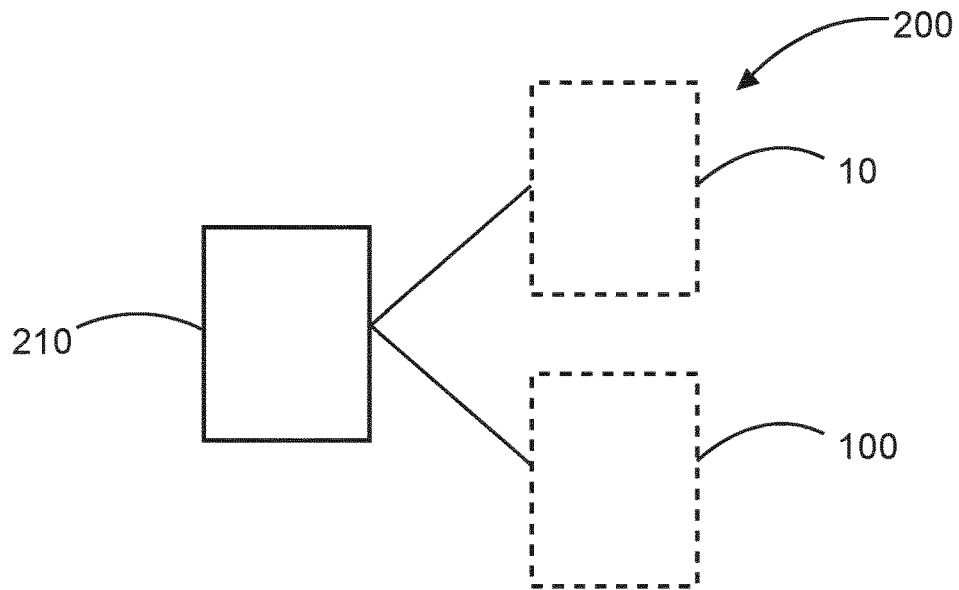
FIG. 3 shows a schematic set up of an example of an image acquisition system.
Figure 4:
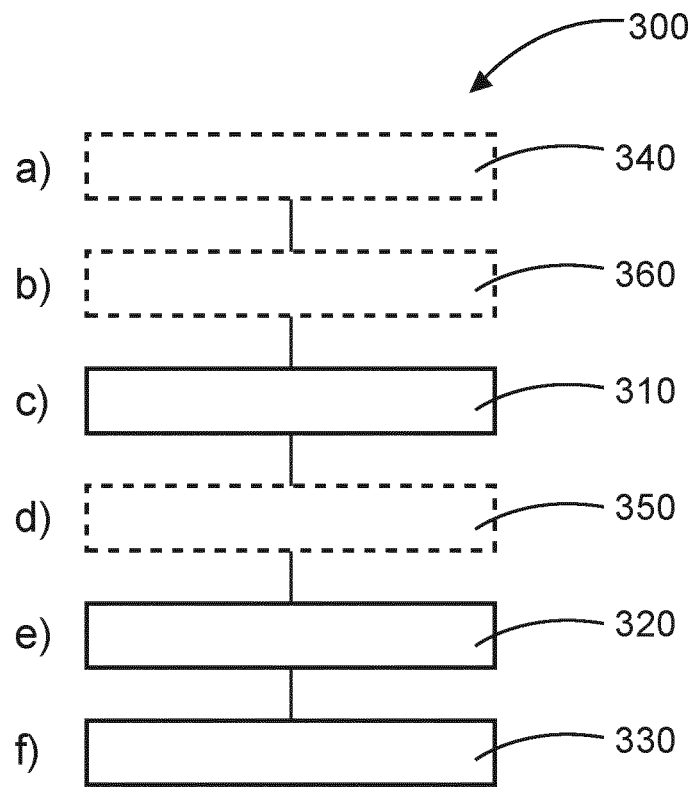
FIG. 4 shows a method for diagnostic image acquisition determination.

FIG. 3 shows an example of an image acquisition system 200. The image acquisition system 200 comprises an image acquisition unit 210, and an apparatus 10 as described with respect to FIG. 1, or a system 100 as described with respect to FIG. 2.

In an example the image acquisition unit is a Magnetic Resonance Imaging (MRI) unit.

In an example the image acquisition unit is a Computer Tomography (CT) unit.

In an example the image acquisition unit is a Positron Emission Tomography (PET) unit.

In an example the image acquisition unit is an X-ray radiography unit.

FIG. 3 shows a method 300 for diagnostic image acquisition in it basic steps where essential steps are shown in solid lines and optional steps are shown in dashed lines. The method comprises:

in a receiving step 310, also referred to as step c), receiving by an input unit a data value relating to at least one biomarker in a measurement blood sample of a patient:

in a determining step 320, also referred to as step e), determining by a processing unit a time to acquire a diagnostic image of the patient, wherein the determining comprises utilizing the data value; and in an outputting step 330, also referred to as step f), outputting by an output unit an indication of the time to acquire the diagnostic image of the patient.

In an example, the data value comprises one or more of: ct-DNA (circulating tumour DNA), CTCs (Circulating Tumour Cells), Exosomes, Platelets.

In an example, the data value comprises a summation of one or more biomarkers.

In an example, the data value comprises a mutant allele frequency.

In an example, the data value comprises a summed mutant allele frequency.

In an example, the baseline data value comprises a sum over mutant allele frequency.

In an example, the data value comprises a summation over all mutant allele frequencies.

In an example, the method comprises step a) receiving 340 by the input unit a baseline data value relating to the at least one biomarker in a baseline blood sample of the patient, and wherein step e) comprises utilizing the baseline data value.

In an example, the baseline data value comprises one or more of: ct-DNA (circulating tumour DNA), CTCs (Circulating Tumour Cells), Exosomes, Platelets. In an example, the baseline data value comprises a summation of one or more biomarkers. In an example, the baseline data value comprises a mutant allele frequency. In an example, the baseline data value comprises a summed mutant allele frequency.

In an example, step e) comprises comparing the data value with at least one threshold data value.

In an example, the method comprises step d) determining 350 by the processing unit at least one threshold data value, wherein the determining comprises utilizing the baseline data value.

In an example, each threshold data value of the at least one threshold data value is calculated as a proportion of the baseline data value.

In an example, step e) comprises determining that the data value is equal to or less than at least one first threshold data value of the at least one threshold data value; or comprises determining that the data value is equal to or greater than a second threshold data value of the at least one threshold data value.

In an example, step d) comprises determining one or more threshold data values indicative of a dimension change or volume change of a tumour of the patient.

In an example, in step d) a threshold data value of the at least one threshold data value is determined as a value indicative of a 30% linear dimension reduction or 66% volume reduction.

In an example, in step d) a threshold data value of the at least one data threshold data value is calculated as 0.34 of the baseline data value.

In an example, in step d) a threshold data value of the at least one threshold data value is determined as a value indicative of a 20% linear dimension increase or 73% volume increase.

In an example, in step d) a threshold data value of the at least one data threshold data value is calculated as 1.73 of the baseline data value; and/or a threshold data value of the at least one data threshold data value is calculated as 1.33 of the baseline data value.

In an example, the method comprises step b) receiving 360 by the input unit imaging resolution information relating to at least one image acquisition unit configured for the diagnostic image acquisition, and wherein in step d) determining one or more threshold data value of the at least one threshold data value comprises utilizing the imaging resolution information.

In an example, the method comprises receiving by the input unit information relating to a size of a tumour of the patient when, or close in time to when, the baseline blood was taken from the patient, and wherein step d) comprises utilization of the size of the tumour.

In an example, in step d) a threshold data value of the at least one data threshold data value is calculated as 0.73 of the baseline data value To monitor therapy response of cancer patients to a therapy (be it a drug therapy, radiation therapy, immunotherapy or a combination of these) in order to determine when to diagnostically image the patient's tumour, the inventors realised that biomarkers in the blood of the patient could be utilised. Tumours release multiple biomarkers in the bloodstream: ct-DNA circulating tumour DNA (originating from dying tumour cells); CTCs circulating tumour cells (shed into the bloodstream from primary tumours and metastases); Exosomes (cell derived vesicles containing tumour mRNA, miRNA, protein and dsDNA); platelets (tumour RNA picked up in circulating platelets). Thus, biomarkers in the blood of the patient come in many forms such as: RBCs; Phagocyte; ct-DNA; normal cf-DNA; circulating tumour cells; healthy cells. Therefore, the inventors realised that using so-called liquid biopsy, determining how a cancer patient is responding to therapy and determining when the patient should undergo an image scan can be done quite simply and effectively from a simple blood draw and analysing the biomarkers in the blood. This is discussed in more detail below.

Figure 5:
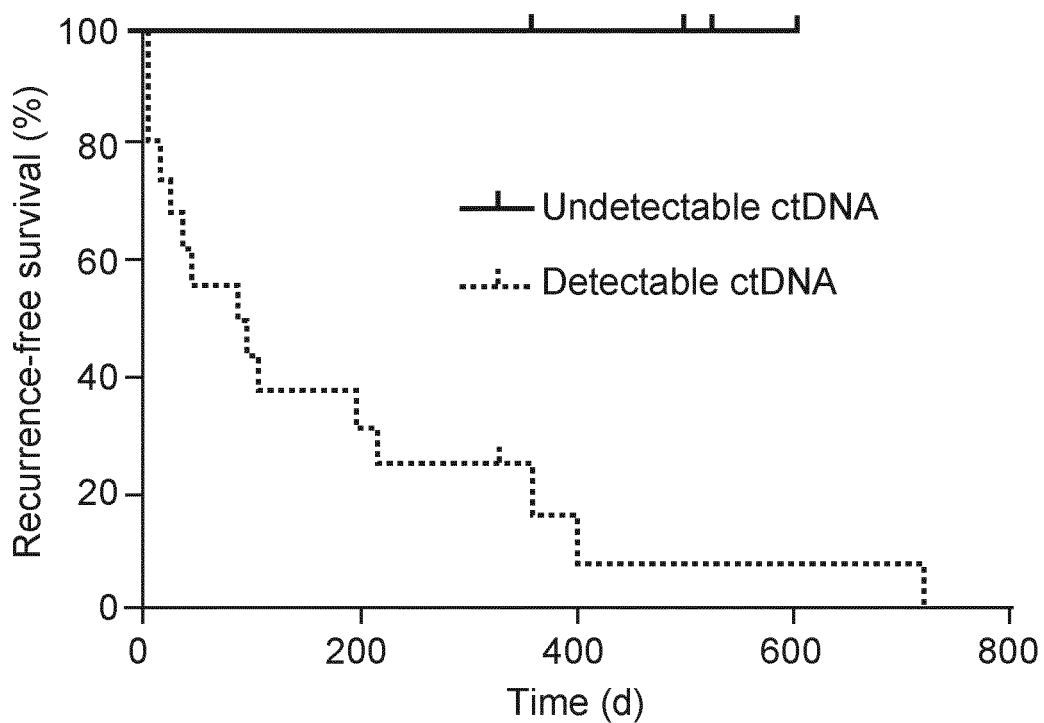
FIG. 5 shows an example of how residual disease after surgery can be detected based on ct-DNA load (this Figure is taken from Diehl et al., Nat. Med 14 (2008) 985)

Currently, so-called circulating tumour DNA (ct-DNA) and circulating tumour cells (CTCs) are clinically the most relevant biomarkers used to monitor therapy response. Of these, ct-DNA is the one which is mostly pursued, as CTCs occur at low count (<10) in most cancer patients unless they have metastatic disease. In the discussion that follows the focus is on ct-DNA, as this is the more prominent of these two and has many important applications; such as determining residual disease after surgery of a primary tumour; see FIG. 5 as an example.

Figure 6:
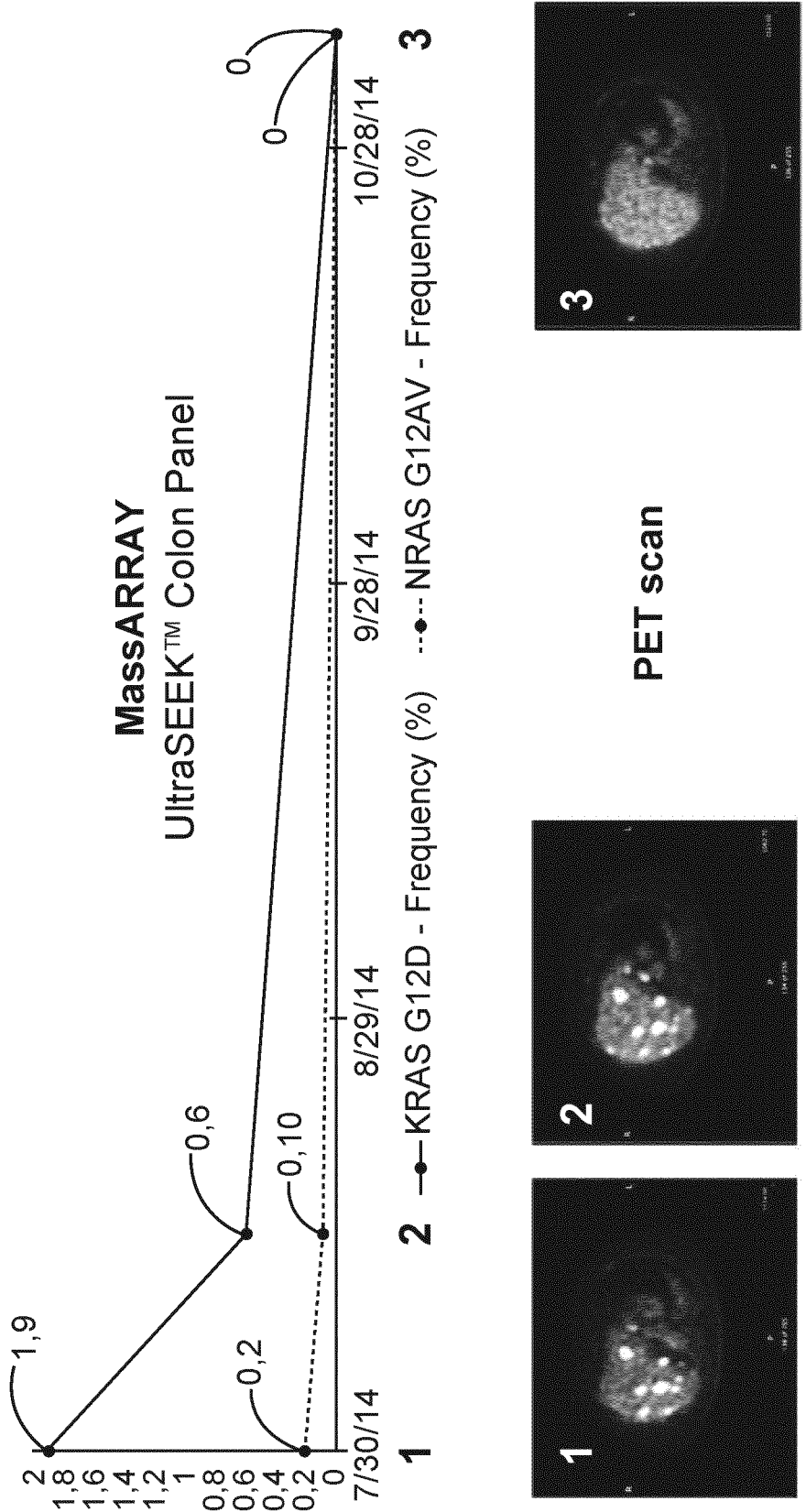
FIG. 6 shows a response to therapy of a colorectal cancer patient as determined by PET scan and by monitoring to mutations (in the KRAS and NRAS genes) using the Agena MassARRAY technology for detecting ct-DNA (Picture courtesy Agena)

Currently, the monitoring of a patient's response to therapy is done using medical imaging equipment such as MRI or CT. Although these methods have the advantage of providing the location of the tumour, it is not always easy to assess a change in tumour volume, as the resolution of medical imaging is typically in the range of mm. Therefore, currently imaging is done at a time when the expectation is that the tumour will have changed by volume or dimension resolvable by imaging systems, but this can be too late for patients who are responding very well to therapy or too late for patients who are not responding well to therapy. The inventors realised that not only does ct-DNA provide molecular information i.e. which mutations in a patient's DNA may be the cause of the cancer and hence which drug to give, ct-DNA provides information enabling a response of the tumour to therapy to be detected much sooner than by imaging. FIG. 6 shows as example.

Figure 7:
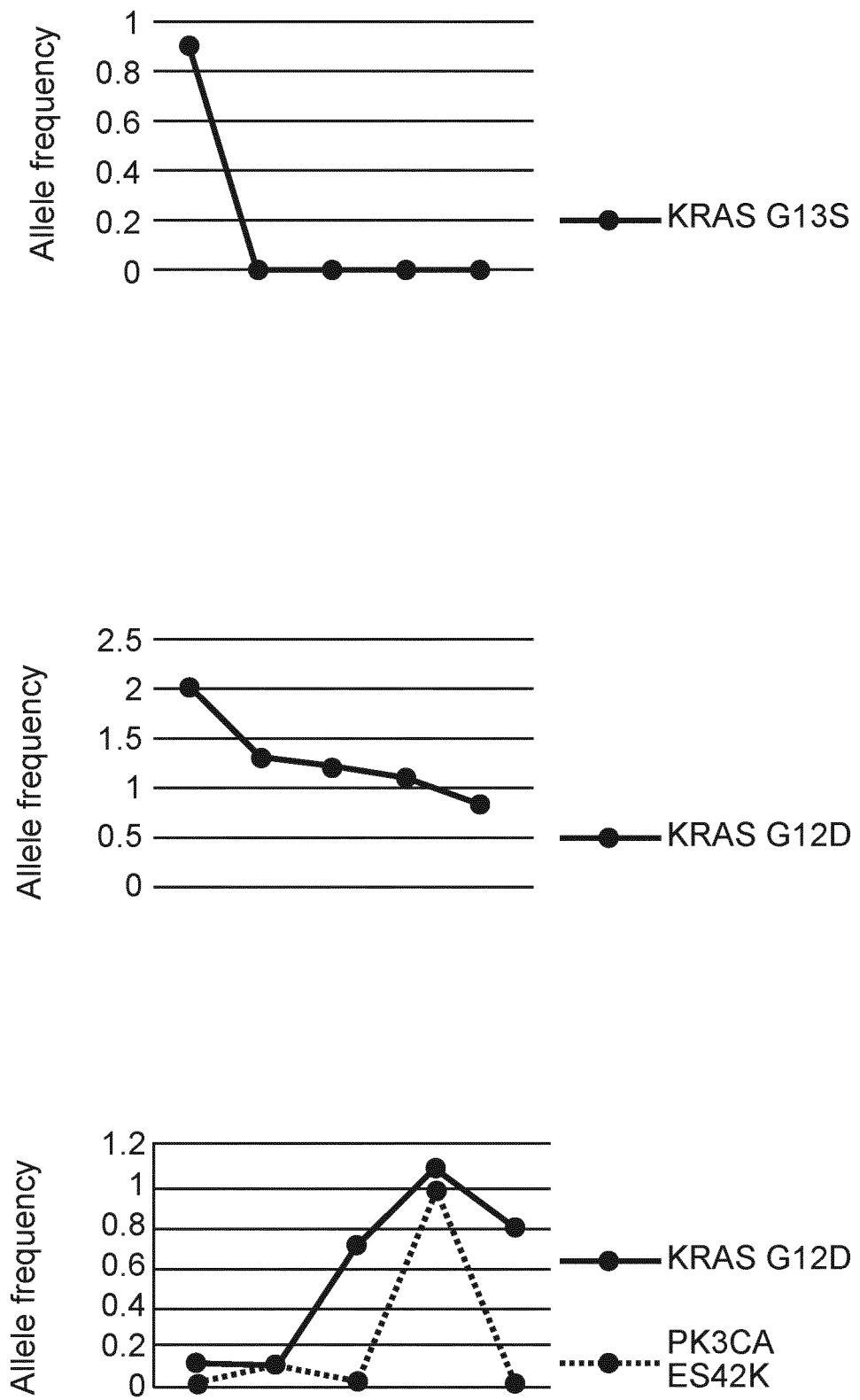
FIG. 7 shows examples of the monitoring of mutant allelic (also termed allele) frequencies (%).

The inventors realised that through the monitoring of mutant allelic frequencies, also termed mutant allele frequencies, (MAF) (%) a patient's response to therapy can be tracked, whether this is to drug therapy, immune-therapy or radiation therapy. It can be determined whether the patient becomes resistant to therapy by the emergence of new mutations. Generally, one can classify, based on mutation response over time, whether a patient is responding to treatment or not. This is shown in FIG. 7. For each of the trends in the ct-DNA allelic frequency i.e. the occurrence of the mutated allele with respect to the normal or wild-type allele, a categorisation can be introduced. For example, if the allelic frequency drops to 0 this can be termed a complete response, if the allelic frequency does not drop to 0 this can be termed a partial response, and where the allelic frequency increases, this can be termed progressive disease.

What the inventors realised was that it would also be possible to determine from the liquid biopsies MAF (%) data whether imaging should be done to confirm therapy response or resistance.

Thus, one can carry out imaging based on a trend in the mutant allelic frequency, or a value compared to an initial start value, as observed in a neo-adjuvant treatment setting (e.g. with the tumour still present prior to surgery). RECIST v1.1 criteria exist [http://www.eortc.be/Services/Doc/RECIST.pdf] that relate to if and when imaging will be capable of detecting a size difference in a tumour, which would be clinically meaningful. For MRI, CT, US imaging modalities the RECIST v1.1 criteria are:

a −30% decrease in linear diameter is the threshold for response, and a +20% increase in an indication for progression.

Such a decrease of 30% in linear diameter would correspond to a 66% volume change (i.e. $(0.7)^3=0.34$, meaning 66% decrease in tumour volume).

The inventors realised that when a primary tumour is present, all (or at least the vast majority) of the mutants stem from the primary tumour. Thus the sum of these $$\sum_{i=1}^{n} MAFi \text{ (at } t = 0)$$

is proportional to the initial tumour size. Then, the value of this sum at later time when that this information is gathered $$t = x, \sum_{i=1}^{n} MAFi \text{ (at } t = x)$$

if it has dropped below 0.34 (1-0.66) that at t=0, this would indicate an expected 66% volume change in the tumour equal to a 30% linear dimension change. Thus, the inventors realised that the biomarker information can be used to determine when to carry out imaging to confirm whether a therapy is successful, because at this time point it is anticipated that the tumour has undergone a change in size that would be clinically meaningful. In this way a patient who might be responding to therapy can undergo an image scan early on to determine whether that patient is a candidate for surgery, thus sparing the patient unnecessary (chemo)-therapy, and giving a cost benefit to the healthcare system. Note by including all mutant allelic frequencies (MAF) in the sums at both time points, a more accurate time determination can be made as mutants may emerge or be suppressed, due to a failing or successful (cytostatic) treatment, respectively.

Furthermore, the inventors realised that the resolution of image acquisition units such as MRI, CT could be taken into account in determining when to acquire an image scan of the patient based on how the biomarker information is changed over time. Thus, typically, in neo-adjuvant therapy, a typical diameter of a tumour will be 3 cm. With an MRI voxel size of 1 mm, at least a 2 mm change in dimension is required to detect reliably a change. That would correspond to a 17% diameter change. CT spatial resolution is higher but lesion conspicuity is lower. For MR and CT, the inventors have determined that a lesion size change of 10% should be reliably detectable. Thus, with respect to the initial tumour (prior to treatment), this would correspond to a 30% volume change (i.e. $(0.9)^3=0.73$ is 27% decrease in tumour volume). Therefore, taking the resolution of the imaging system into account for standard sized tumour, a reduction in the sum of biomarkers (such as MAF) if it has fallen to 73% of the initial value would indicate that a dimension change of the tumour would now be resolvable by the imaging system. If, an initial imaging scan of the tumour is undertaken at an onset point of therapy when biomarker information is also acquired, then the actual size of the tumour can be input (at t=0) into the above detailed calculation in order to determine exactly what fall in biomarker count is required for the dimension change of the tumour to now be resolvable by an imaging system.

Furthermore, the inventors realised that biomarker information can also be used for predicting measure of disease progression and determining when and image scan of the patient should be carried out. As detailed above, the RECIST criteria indicated that a 20% increase in diameter of a tumour would indicate progression. This corresponds to a volume increase of $(1.2)3=1.73$. Accordingly, an increase in biomarker number from a starting position of 73% can be used to trigger the point at which the patient should be imaged in order to confirm that the tumour is progressing, enabling an early change of therapy for that patient. However, the inventors predict that in the future it could be found that for certain tumours of certain types (for example HER2 positive breast cancer) the correlation between total sum of the allelic frequencies is stronger than for others cancers, for example certain colon cancers. Thus, the biomarker information can in some examples can be utilised in the form of a sum over all allelic frequencies, but in examples it is anticipated that the biomarker information for some (one or more) molecular subtypes can be restricted to some (a more limited set) of mutant allelic frequencies associated with this molecular subtype of cancer and could better be used to predict when imaging could be undertaken.

SUMMARY

A patient should be imaged to conform that the patient is responding to therapy when:

$$\sum_{i=1}^{n} MAFi \text{ (at } t = x) \leq \alpha 1 \sum_{i=1}^{n} MAFi \text{ (at } t = 0) \text{ with } 0 \leq \alpha_1 \leq 0.34$$

Here, $MAF_i$ denotes the mutant allele frequency (in %) of genetic modification i, as a function of time.

A patient can be imaged earlier, to account for resolution of the imaging system, where the situation below is detailed for a nominal starting tumour size of 3 cm, thus imaged when:

$$\sum_{i=1}^{n} MAFi \text{ (at } t = x) \leq \alpha 2 \sum_{i=1}^{n} = MAFi \text{ (at } t = 0) \text{ with } \alpha_2 < 0.73$$

This also suggests that in addition to imaging being carried out at this time point, the mutant allele frequency can be used to determine that a patient is responding to therapy. Thus far, imaging is the 'gold standard' for determining this, but could be replaced by the monitoring of MAF or biomarker values.

Furthermore, a prediction based on liquid biopsy information can be made to determine when to carry out imaging to confirm that a patient is not responding $$\sum_{i=1}^{n} MAFi \text{ (at } t = x) \geq \beta \sum_{i=1}^{n} = MAFi \text{ (at } t = 0) \text{ with } \beta \geq 1.33$$

Also, it will be appreciated that the change in mutant allele frequency over time can be used to predict a mutant allele frequency into the future, thereby enabling a time at which to diagnostic image the patient to be determined.

In another exemplary embodiment, a computer program or computer program element is provided that is characterized by being configured to execute the method steps of the method according to one of the preceding embodiments, on an appropriate apparatus or system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for diagnostic image acquisition, comprising:
   an input unit;
   a processing unit; and
   an output unit;
   wherein, the input unit is configured to receive a data value relating to at least one biomarker in a measurement blood sample of a patient;
   wherein, the processing unit is configured to determine an optimum time to acquire diagnostic imagery of a patient from information form utilizing the data value relating to the biomarker; and
   wherein, the output unit is configured to output an indication of the time to acquire the diagnostic image of the patient.

2. Apparatus according to claim 1, wherein the input unit is configured to receive a baseline data value relating to the at least one biomarker in a baseline blood sample of the patient, and wherein the determination of the time to acquire the diagnostic image comprises utilization of the baseline data value.

3. Apparatus according to claim 1, wherein the determination of the time to acquire the diagnostic image comprises a comparison of the data value with at least one threshold data value.

4. Apparatus according to claim 3, wherein:
   the input unit is configured to receive a baseline data value relating to the at least one biomarker in a baseline blood sample of the patient, and wherein the determination of the time to acquire the diagnostic image comprises utilization of the baseline data value, and
   the processing unit is configured to determine the at least one threshold data value, wherein the determination of the at least one threshold data value comprises utilization of the baseline data value.

5. Apparatus according to claim 4, wherein each threshold data value of the at least one threshold data value is calculated as a proportion of the baseline data value.

6. Apparatus according to claim 3, wherein the determination of the time to acquire the diagnostic image comprises a determination that the data value is equal to or less than at least one first threshold data value of the at least one threshold data value; or wherein the determination of the time to acquire the diagnostic image comprises a determination that the data value is equal to or greater than a second threshold data value of the at least one threshold data value.

7. Apparatus according to claim 4, wherein the determination of the at least one threshold data value comprises a determination of one or more threshold data values indicative of a dimension change or volume change of a tumour of the patient.

8. Apparatus according to claim 4, wherein a threshold data value of the at least one data threshold data value is calculated as 0.34 of the baseline data value.

9. Apparatus according to claim 4, wherein a threshold data value of the at least one data threshold data value is calculated as 1.73 of the baseline data value; and/or a threshold data value of the at least one data threshold data value is calculated as 1.33 of the baseline data value.

10. Apparatus according to claim 3, wherein the input unit is configured to receive imaging resolution information relating to at least one image acquisition unit configured for the diagnostic image acquisition, and wherein determination of one or more threshold data value of the at least one threshold data value comprises utilization of the imaging resolution information.

11. Apparatus according to claim 4, wherein a threshold data value of the at least one data threshold data value is calculated as 0.73 of the baseline data value.

12. A system for diagnostic image acquisition, comprising:
- an analysis unit; and
- an apparatus according to claim 1;
- wherein, the analysis unit is configured to analyze a blood sample of a patient and determine a data value relating to at last one biomarker in the blood sample.

13. An image acquisition system, comprising:
- an image acquisition unit; and
- the apparatus according to claim 1.

14. A method for diagnostic image acquisition, comprising:
- receiving by an input unit a data value relating to at least one biomarker in a measurement blood sample of a patient;
- determining by a processing unit a time to acquire a diagnostic image of the patient, wherein the determining comprises utilizing the data value; and
- outputting by an output unit an indication of the time to acquire the diagnostic image of the patient.

15. A non-transitory machine-readable medium encoded with instructions for execution by a processor, the medium comprising:
- instructions for receiving by an input unit a data value relating to at least one biomarker in a measurement blood sample of a patient;
- instructions for determining by a processing unit a time to acquire a diagnostic image of the patient, wherein the determining comprises utilizing the data value; and
- instructions for outputting by an output unit an indication of the time to acquire the diagnostic image of the patient.

* * * * *